United States Patent
Enomura

(10) Patent No.: US 11,583,823 B2
(45) Date of Patent: Feb. 21, 2023

(54) FORCED THIN FILM-TYPE FLOW REACTOR AND METHOD FOR OPERATING SAME

(71) Applicant: M. TECHNIQUE CO., LTD., Izumi (JP)

(72) Inventor: Masakazu Enomura, Izumi (JP)

(73) Assignee: M. TECHNIQUE CO., LTD., Izumi (JP)

( * ) Notice: Subject to any disclaimer, the term of this patent is extended or adjusted under 35 U.S.C. 154(b) by 596 days.

(21) Appl. No.: 16/616,821

(22) PCT Filed: May 30, 2017

(86) PCT No.: PCT/JP2017/020121
§ 371 (c)(1),
(2) Date: Nov. 25, 2019

(87) PCT Pub. No.: WO2018/220719
PCT Pub. Date: Dec. 6, 2018

(65) Prior Publication Data
US 2021/0170358 A1    Jun. 10, 2021

(51) Int. Cl.
*B01J 19/18* (2006.01)
*A61L 2/07* (2006.01)
(Continued)

(52) U.S. Cl.
CPC ............ *B01J 19/1887* (2013.01); *A61L 2/07* (2013.01); *A61L 2/26* (2013.01); *B01J 19/0006* (2013.01);
(Continued)

(58) Field of Classification Search
CPC ............... B01J 19/1887; B01J 19/0006; B01J 2219/00162; B01J 2219/00247;
(Continued)

(56) References Cited

U.S. PATENT DOCUMENTS

| | | |
|---|---|---|
| 6,517,077 B1 | 2/2003 | Enomura |
| 2010/0155310 A1 | 6/2010 | Enomura |
| 2014/0134068 A1 | 5/2014 | Enomura |

FOREIGN PATENT DOCUMENTS

| | | |
|---|---|---|
| JP | 2001-21045 A | 1/2001 |
| JP | 2009-82902 A | 4/2009 |

(Continued)

OTHER PUBLICATIONS

International Search Report, issued in PCT/JP2017/020121, dated Sep. 5, 2017.

*Primary Examiner* — Lessanework Seifu
(74) *Attorney, Agent, or Firm* — Birch, Stewart, Kolasch & Birch, LLP

(57) ABSTRACT

A forced thin film-type flow reactor is provided with a clearance adjustment mechanism that allows the clearance to be set and adjusted by an alternative means. The flow reactor processes a fluid to be processed by passing the fluid to be processed between a first processing surface and a second processing surface capable of moving towards and away from each other, and the flow reactor comprises a pressure balancing mechanism and a mechanical clearance mechanism. The pressure balancing mechanism forms a minute first clearance by providing pressure balance between the pressure applied by the fluid to be processed, which acts in the direction in which the first processing surface and the second processing surface move away from each other, and a force produced by a back pressure mechanism, which acts in the direction in which the first processing surface and the second processing surface move towards each other.

17 Claims, 4 Drawing Sheets

(51) Int. Cl.
  *A61L 2/26* (2006.01)
  *B01J 19/00* (2006.01)
  *B08B 3/04* (2006.01)
  *B08B 13/00* (2006.01)

(52) U.S. Cl.
  CPC ............... *B08B 3/04* (2013.01); *B08B 13/00* (2013.01); *A61L 2202/17* (2013.01); *B01J 2219/00162* (2013.01); *B01J 2219/00247* (2013.01)

(58) Field of Classification Search
  CPC ..... B01J 2219/00788; B01J 2219/0093; A61L 2/07; A61L 2/26; A61L 2/18; A61L 2202/17; B08B 3/04; B08B 13/00; B08B 9/00
  See application file for complete search history.

(56) References Cited

FOREIGN PATENT DOCUMENTS

| | | |
|---|---|---|
| JP | 2009-214056 A | 9/2009 |
| JP | 2009-255083 A | 11/2009 |
| JP | 2012-228666 A | 11/2012 |
| JP | 2013-39567 A | 2/2013 |
| JP | 5305480 B2 | 10/2013 |
| JP | 2015-213870 A | 12/2015 |

(A)

(B)

FORCED THIN FILM-TYPE FLOW REACTOR AND METHOD FOR OPERATING SAME

TECHNICAL FIELD

The present invention relates to an improvement of a microreactor, in particular, it relates to an improvement of a flow reactor which employs a circular flow path defined between processing surfaces which rotate relatively as a flow path for performing fluid processing in a macroreactor.

BACKGROUND ART

A microreactor is an apparatus for performing a chemical reaction, a stirring operation, or the like, in a space with a side length of 1 mm or less, uses a microchannel in many cases. It has been researched and developed in the field of microprocess engineering for about 20 years, and it has recently been also used as an actual producing machine. A microreactor is not a so-called batch type reactor using a large-scale tank and the like, but a continuous type reaction apparatus, and is excellent in energy efficiency, reaction rate, yield, safety, and so on as compared with the batch type apparatus performing a larger scale reaction (Patent Document 1).

However, it is difficult to scale up the microreactor, so that numbering up, that is, small-sized microreactors are connected with a necessary number and used for actual production. However, a general microreactor uses a microchannel, so that it is difficult to apply the general microreactor for a reaction accompanied with solid separation, a reaction which generates a gas, or a fluid processing for a material to be processed having a high viscosity, thus there is a problem that choices of the material to be processed are few (Patent Documents 2 and 3).

In order to solve these problems, apparatuses such as those disclosed in Patent Document 4 or Patent Document 5 have been recently used in many cases. This apparatus is provided with a space between at least two processing surfaces which rotate relative to the other, and the two processing surfaces are disposed so as to be capable of moving towards and apart from each other in the axial direction of the rotation. By maintaining a minute clearance between the two processing surfaces, introducing at least two or more of the fluids to be processed into between the two processing surfaces maintained the minute clearance to form a forced thin film, and thus mixing, stirring and reacting in the forced thin film, the apparatus can be used for reactions accompanied with solid separation or generation of gas, or a process of a material to be processed having high viscosity, and thus an objective uniform substance can be obtained.

As a characteristic feature of this apparatus, there may be mentioned a point that the processing is performed in a state that a fluid to be processed is made a thin film fluid with, for example, a film thickness of 1 mm or less by passing the fluid to be processed which is pressurized by a fluid pressure imparting mechanism through an circular flow path formed between processing surfaces arranged so as to be able to opposite to each other.

This apparatus is not only be able to be used for a fluid processing method such that the processing is performed by passing one kind of a fluid as a fluid to be processed from an inside to an outside of an circular flow path to form a thin film fluid with one kind of a fluid, but also for a fluid processing method such that the processing is performed by forming a thin film fluid with a plural kind of fluids. When the plural kind of fluids (for example, a first fluid and a second fluid) are used, the processing is performed in the state that a thin film fluid is formed by a first fluid by passing the first fluid from the inside to the outside of the circular flow path, and the second fluid is introduced from the middle of the circular flow path to join the second fluid to the thin film fluid of the first fluid, whereby the two kinds of the fluids are made a thin film fluid as the fluid to be processed.

Specifically, in Patent Document 5, it is said that with regard to an apparatus in which a surface-approaching pressure imparting mechanism for applying a surface-approaching pressure between both processing surfaces is provided, a minute clearance between the both processing surfaces is maintained by balancing a separating force acting in the direction of move away from the both processing surfaces to each other at the time of passing the fluid to be processed through between the both processing surfaces which rotate relative to the other and a surface-approaching pressure via the fluids to be processed inbetween the processing surfaces, the fluid to be processed introduced from an introduction part and the fluid to be processed introduced from a supply flow path are passed between the both processing surfaces as a fluid film thereby subjecting to the process to these fluid to be processed, the separating force is defined by at least one kind selected from the group consisting of a centrifugal force generated by relative rotation of a first processing surface and a second processing surface, a negative pressure when the negative pressure is applied as a surface-approaching pressure, property of the fluid to be processed, and a dynamic pressure which is a dynamic pressure generated in a groove-like depression formed in at least one of the both processing surfaces, wherein the dynamic pressure is generated by extending the groove-like depression from the upstream side of the end portion to the downstream side of the first processing surface or the second processing surface.

It is disclosed that the surface-approaching pressure is to apply a force in the direction of approaching the first processing surface and the second processing surface into close to each other and may be constituted by at least any one of a pressure device for fluid pressure (positive pressure) such as spring, air pressure and hydraulic pressure, and pressure-receiving surfaces for approaching which act in the direction of approaching the both processing surfaces into close by receiving predetermined pressure applied to the fluid to be processed.

However, in the apparatuses disclosed in Patent Document 4 and Patent Document 5, they are intended to be used as a reactor or various fluid processing apparatuses by setting a distance between processing surfaces to a minute distance such as 1 mm or less. Therefore, it has not been disclosed a means necessary for separating the both processing surfaces at a relatively large distance. Theoretically, when the pressure of the fluid to be passed between the both processing surfaces is increased, separating force becomes large and it is possible to make the distance between both processing surfaces large, but it is not expected to operate the apparatus with such a higher pressure and mechanical safety is not guaranteed.

In particular, even if it is investigated to adjust the clearance between the both processing surfaces by air or vacuum force in addition to the pressure of the fluid to be processed, for increasing the clearance between the both processing surfaces, in addition to increasing the strength of pressure resistant of the apparatus as a matter of course, it naturally requires equipment such as piping, regulating valves, and pressure monitoring, so that it is unavoidable to be a large and heavy equipment facility.

Thus, in Patent Document 4 and Patent Document 5, neither specific means nor technical idea to set a large clearance markedly exceeding a clearance which is set during the reaction as a reactor is disclosed.

On the other hand, when CIP (Cleaning in Place: fixed cleaning) or SIP (Sterilizing in Place: stationary sterilization) is performed, it is necessary to secure a flow amount of a cleaning liquid or pure steam for sterilization in each part of the apparatus. However, it is impossible to increase the pressure of the cleaning liquid or the pure steam for sterilization to infinity, and in the apparatuses according to Patent Document 4 and Patent Document 5 in which the clearance depends on the pressure of the fluid passing through the space between the both processing surfaces, there was a problem that the since clearance had to be narrow and the flow amount of the cleaning liquid or the pure steam for sterilization cannot be ensured, the temperature rise required for sterilization was difficult, and a time required for the cleaning takes markedly long.

In addition, when the processed material or reaction product in the fluid to be processed is adhered to the processing surface, it is necessary to disassemble the apparatus and remove the adhered materials from the processing surface, so it requires too much time and effort for disassemble and reassemble of the apparatus.

PRIOR ART DOCUMENTS

Patent Documents

Patent Document 1: Japanese Patent Laid-Open Publication No. 2009-214056
Patent Document 2: Japanese Patent Laid-Open Publication No. 2012-228666
Patent Document 3: Japanese Patent Laid-Open Publication No. 2009-255083
Patent Document 4: Japanese Patent Laid-Open Publication No. 2009-082902
Patent Document 5: Japanese Patent Publication No. 5,305,480

DISCLOSURE OF THE INVENTION

Problems to be Solved by the Invention

An object of the present invention is, in a flow reactor which performs processing of fluid to be processed by passing the fluid to be processed between two processing surfaces disposed so as to be relatively capable of moving towards and away from each other, to provide a forced thin film-type flow reactor provided with, in addition to a pressure balancing mechanism which sets and adjusts the clearance between processing surfaces due to pressure balance, a clearance adjustment mechanism that allows the clearance to be set and adjusted by an alternative means.

In addition, another object of the present invention is to provide a forced thin film-type flow reactor which allows to set and adjust the clearance between processing surfaces irrespective of a pressure of a fluid for cleaning and sterilization such as a cleaning liquid and pure steam for sterilization when performing CIP (Cleaning in Place: fixed cleaning) or SIP (Sterilizing in Place: stationary sterilization), and can ensure a flow amount of the fluid for cleaning and sterilization required for the processing, and a method for operating the same.

Still another object of the present invention is to provide a forced thin film-type flow reactor capable of removing the adhered material from the processing surface without disassembling the apparatus even when the processed material or reaction product in the fluid to be processed is adhered to the processing surface.

Means to Solve the Problems

The present invention solved the problems by the following means in a flow reactor for performing processing of a fluid to be processed by passing the fluid to be processed between the two processing surfaces disposed so as to be relatively capable of moving towards and away from each other.

The forced thin film-type flow reactor according to the present invention comprises;
A: a pressure balancing mechanism which forms first minute clearance between the two processing surfaces by a pressure balance between imparted pressure of the fluid to be processed which acts in the direction of move away from at least one of the processing surface and a force due to back pressure mechanism which acts in the direction of approaching to the at least one of the processing surface, and
B: a mechanical clearance mechanism which mechanically sets a second clearance being greater than the first clearance between the two processing surfaces.

In the execution of the present invention, a cleaning and sterilization flow path for CIP or SIP capable of being connectable between two processing surfaces is provided, and further, the cleaning and sterilization flow path is set at a position where the path is closed in a first clearance as the processing surfaces approaches to and separates from and at a position where the path is opened in a second clearance, whereby a sufficient flow amount of various fluids for cleaning and sterilization may be supplied between the two processing surfaces.

In addition, in the execution of the present invention, it is preferable that the first clearance set by pressure balancing mechanism of A be 0.5 to 50 μm, the second clearance set by mechanical clearance mechanism of B be 50 μm to 4 mm, and the mechanical clearance mechanism of B be so constituted that the second clearance be set to be a greater value than that of the first clearance set by the pressure balancing mechanism of A irrespective of the pressure of the fluid passed between the two processing surfaces.

Further, the present invention may be executed that a first processing member and a second processing member are provided, the processing surfaces are disposed at the surfaces of the first processing member and the second processing member which they are faced with each other, the second processing member is connected to the second holder capable of approaching to and separating from through the back pressure mechanism, the second processing member is arranged so as to be able to approach to the first processing member by separating from the second holder and so as to be able to separate from the first processing member by approaching to the second holder, and further, the second holder is made as a second elevating holder which approaches to and separates from the first processing member. The mechanical clearance mechanism is preferably constituted such that the second elevating holder is mechanically moved so as to be able to approach to and separate from the first processing member, and when the second elevating holder moves in the direction of separating from the first processing member, the second processing member with the second elevating holder are mechanically moved in the direction of mechanically separating from the first processing member.

Moreover, the present invention is to provide a method for operating the forced thin film-type flow reactor, and in the operating method, when the material to be processed is processed, processing of the fluid to be processed is performed by passing the fluid to be processed between the two processing surfaces set at the first clearance, and at the time of CIP or SIP of the forced thin film-type flow reactor, CIP or SIP is performed by the second clearance.

Effects of the Invention

The present invention is provided, in a flow reactor for performing processing of a fluid to be processed by passing the fluid to be processed between two processing surfaces disposed so as to be capable of relatively moving towards and away from each other, a forced thin film-type flow reactor with which provided a clearance adjustment mechanism that allows set and adjust the clearance by an alternative means in addition to a pressure balancing mechanism in which the clearance between processing surfaces is set and adjusted by pressure balance.

Further, the present invention may be provided the forced thin film-type flow reactor and the method for operating same, wherein when performing CIP (Cleaning in Place: fixed cleaning) or SIP (Sterilizing in Place: stationary sterilization), the clearance between processing surfaces can set and adjust irrespective of a pressure of a fluid for cleaning and sterilization such as a cleaning liquid and pure steam for sterilization and ensure a flow amount of the fluid for cleaning and sterilization required for the processing. In particular, it could be provided an apparatus which can perform CIP or SIP with simple mechanism not requiring a large separate apparatus without disassembling the apparatus.

The present invention could be provided the forced thin film-type flow reactor which is capable of separating between processing surfaces readily and forcedly without disassembling the apparatus in the case that the processing surfaces could not be separated due to the adhesion of the processed material or the reaction product in the fluid to be processed between the processing surfaces.

EMBODIMENTS TO CARRY OUT THE INVENTION

Figure 1:
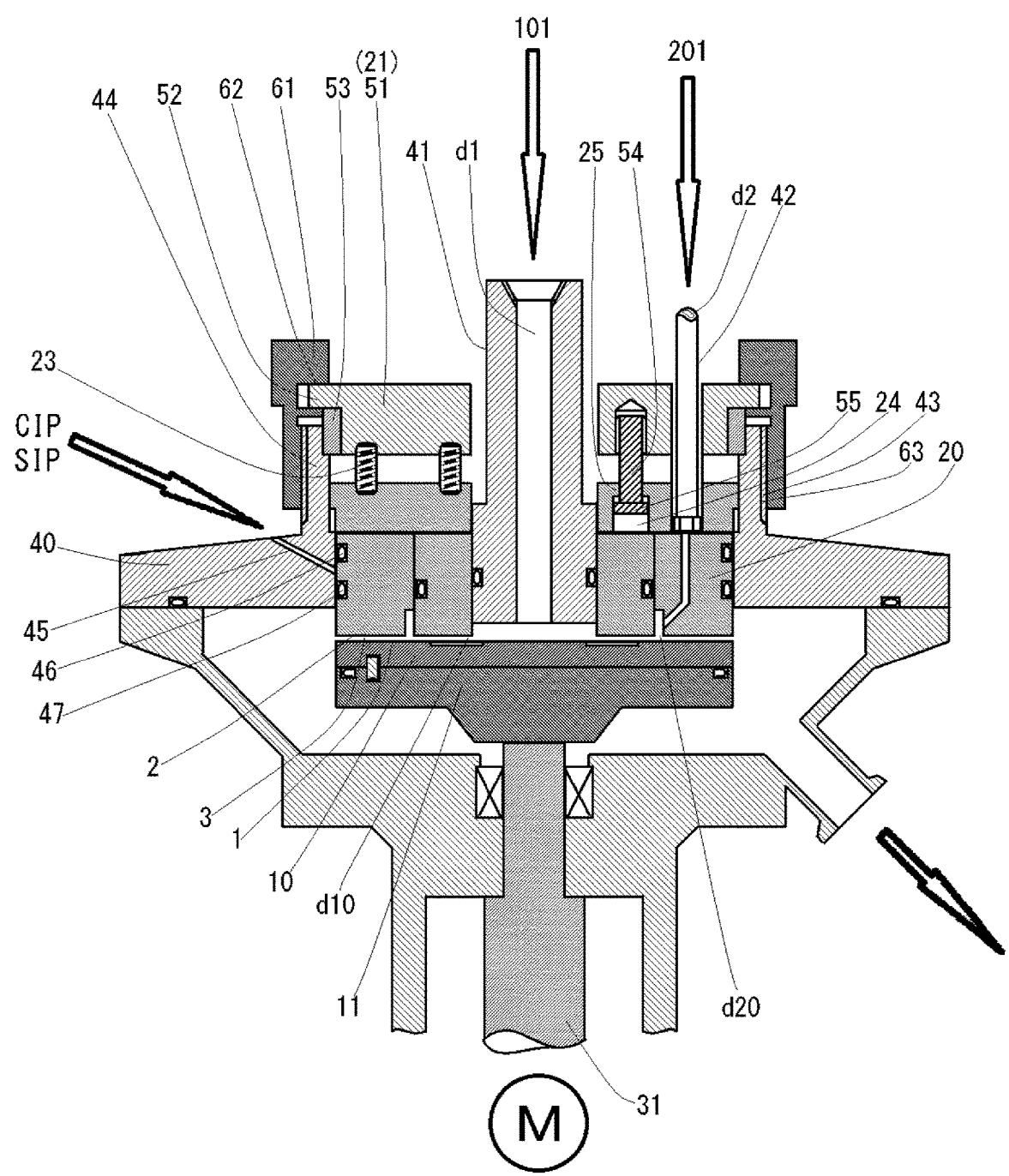
FIG. 1 is a schematic cross-sectional view showing an embodiment at the time of setting the first clearance in a fluid processing apparatus used for a fluid processing method according to an embodiment of the present invention.

Hereinunder, embodiments of the present invention will be explained by using the drawings.

The fluid processing apparatus according to the present invention is provided with a first fluid pressure imparting mechanism 101 for supplying a first fluid with a predetermined pressure, and a second fluid pressure imparting mechanism 201 for supplying a second fluid with a predetermined pressure.

It is suitable that the first fluid and the second fluid to be fed are each subjected to processing such as mixing, stirring, dispersion, emulsification, reaction, etc., to adjust the composition and properties of substances constituting the supplied fluid, or to set the most suitable temperature for the reaction conditions.

(With Regard to Pressure Imparting Mechanism)

The fluids to be processed (in this example, the first fluid and the second fluid) which have undergone these preparation processes are supplied to the fluid processing apparatus by the first fluid pressure imparting mechanism 101 and the second fluid pressure imparting mechanism 201. Various pumps not shown in the drawings can be used for the first fluid pressure imparting mechanism 101 and the second fluid pressure imparting mechanism 201. Moreover, in order to suppress occurrence of pulsation at the time of pressure feeding, a pressure imparting device provided with a pressurized container may be employed. A gas for pressurization is introduced into the pressurized container which the fluid to be processed is stored, and the fluid to be processed is pushed out by the pressure so that the fluid to be processed can be fed by the pressure.

(With Regard to Fluid Processing Apparatus)

The main body of the fluid processing apparatus will be explained by using FIG. 1 to FIG. 4.

The form of the part which directly performs the reaction process in this fluid processing apparatus is the same as those of the apparatus described in Patent Document 4 and Patent Document 5. Specifically, the fluids to be processed are processed in an circular flow path formed between the processing surfaces in processing members disposed so as to be capable of approaching to and separating from each other, which rotates relative to the other. This apparatus is to perform continuous reaction process wherein of the fluids to be processed, the first fluid of the first fluid to be processed is introduced between processing surfaces, the second fluid of second fluid to be processed is introduced between processing surfaces from another flow path having an opening part leading to between the processing surfaces independent from the flow path into which the above fluid is introduced, and the first fluid and the second fluid are mixed therebetween the processing surfaces. In other words, it is an apparatus in which the above-mentioned respective fluids are joined in the circular flow path formed between the disk-shaped processing surfaces opposed in the axial direction to form a thin film fluid, whereby the above-mentioned reaction process of the fluid to be processed is performed in the thin film fluid. Incidentally, this apparatus is most suitable for processing plurality of fluids to be processed but also can be used for processing single fluid to be processed in the circular flow path. Further, as the plurality of fluids to be processed, in addition to the second fluid, more fluids such as third, fourth fluids can be supplied as the fluids to be processed, and accordingly, it can be performed as an apparatus having many flow paths independent from each other.

Figure 3:
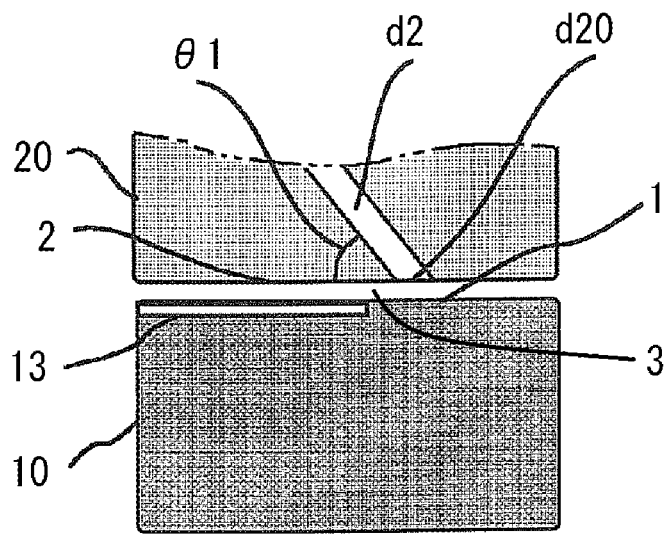
FIG. 3(A) is a cross-sectional view of second introduction part of the apparatus.
FIG. 3(B) is an enlarged view of a main part of the processing surface for explaining the second introduction part.
Figure 3:
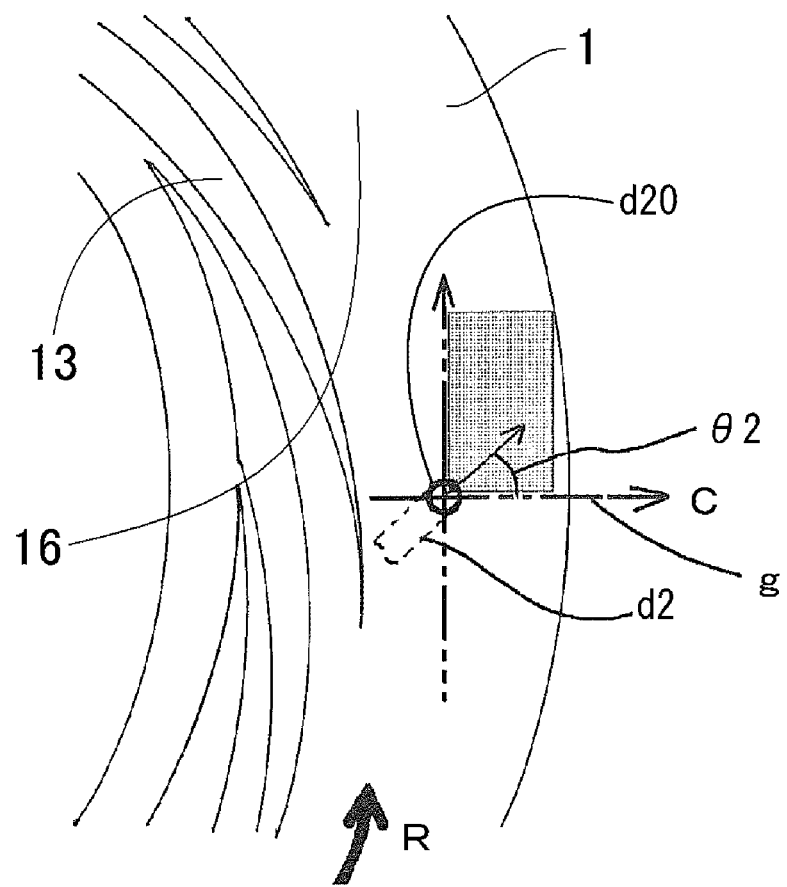
Figure 4:
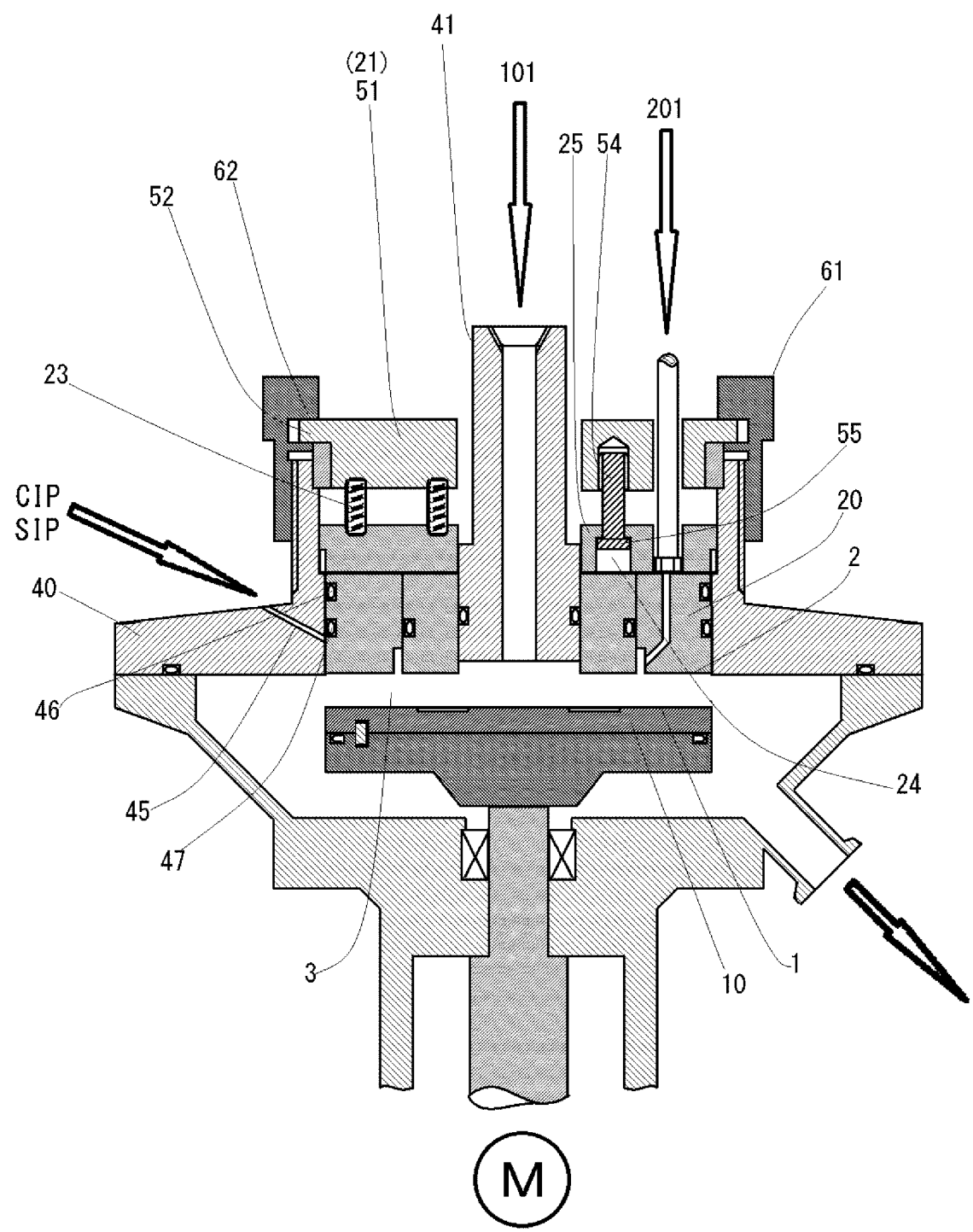
FIG. 4 is a schematic cross-sectional view showing an embodiment at the time of setting the second clearance in the fluid processing apparatus.

In FIG. 1, FIG. 3 and FIG. 4, the top and bottom of the figure correspond to the top and bottom of the apparatus, but in the present invention, it merely indicates the relative positional relation among all the directions such as the top, bottom, front, back, left and right and does not specify an absolute position. Also, in these drawings, the top and bottom coincide with the relative movement direction of the processing surface while approaching to and separating from, in the second processing member 20, the bottom side is the direction of approaching, and the in the second processing member 20, top side is the direction of separating.

In FIG. 2(A) and FIG. 3(B), reference character "R" indicates the direction of rotation. In FIG. 3(B), reference character "C" indicates a direction of centrifugal force (a radial direction).

The fluid processing apparatus according to the present invention is in common with the apparatus disclosed in Patent Document 4 and Patent Document 5 at the point of that A: a pressure balancing mechanism which forms minute clearance between the two processing surfaces by a pressure balance between imparted pressure of the fluid to be processed which acts in the direction of move away from at least one of the processing surface and a force due to back pressure mechanism which acts in the direction of approaching to the at least one of the processing surface, but different from the apparatus disclosed in Patent Document 4 and Patent Document 5, in addition to the above, at the point that B: a mechanical clearance mechanism which mechanically sets the clearance between the two processing surfaces is provided.

The present invention is assumed on the technology in which the pressure balancing mechanism and the circular flow path that are in common to the apparatuses disclosed in these prior art documents, explanations related to these parts (in other words, explanations of processing to the fluid to be processed under the first minute clearance condition) are performed in advance.

(With Regard to Processing Surface)

This fluid processing apparatus is provided with a first processing member 10 and a second processing member 20 which are opposed to each other, and at least one of the processing members rotates. The opposing surfaces of the first processing member 10 and the second processing member 20 are the processing surfaces, respectively, and the first processing member 10 is provided with a first processing surface 1 and the second processing member 20 is provided with a second processing surface 2.

The both processing surfaces 1 and 2 define an circular flow path 3 and subject to processing such as a reaction to the fluid to be processed supplied from a first fluid pressure imparting mechanism 101 and a second fluid pressure imparting mechanism 201.

A distance between the both processing surfaces 1 and 2 can be appropriately changed to perform and is usually adjusted to a minute clearance (first clearance) of 1 mm or less, for example, from about 0.5 µm to 50 µm. By this mentioned above, the fluid to be processed passing through between the both processing surfaces 1 and 2 becomes a forced thin film fluid due to the force of the both processing surfaces 1 and 2.

When plurality of the fluids to be processed containing the first fluid and the second fluid are processed by using the fluid processing apparatus, the fluid processing apparatus is connected to the flow path for the first fluid, and the fluids to be processed are introduced from an upper stream end (in this example, inner side of the circular flow path) of the circular flow path 3 defined by the both processing surfaces 1 and 2. In addition, this circular flow path 3 forms a part of the flow path for the second fluid, different from that of the first fluid. Then, in the circular flow path 3 between the both processing surfaces 1 and 2, processing of the fluids is performed such as both of the fluids to be processed of the first fluid and the second fluid are mixed and reacted, and the like.

When it is specifically explained, the fluid processing apparatus is provided with a first holder 11 holding the first processing member 10, a second holder 21 holding the second processing member 20, a back pressure mechanism, a rotation drive mechanism M, a first introduction part d1 and a second introduction part d2, and the first fluid and the second fluid are introduced into the circular flow path 3 in the state that predetermined pressure is set by the above-mentioned first fluid pressure imparting mechanism 101 and the second fluid pressure imparting mechanism 201 which become a fluid pressure imparting mechanism.

As shown in FIG. 2(A), in this embodiment, the first processing member 10 is a circular body, specifically a disk with a ring form. In addition, the second processing member 20 is also a ring-shaped disk, further may be a disk shape having not being provided with an opening at the center under the condition that the fluid to be processed including the first fluid and the second fluid can be introduced.

The first processing member 10 and the second processing member 20 may be constituted by a single member or combination of plurality of members, and the material thereof is not only metal, but also ceramics, sintered metal, abrasion-resistant steel, sapphire, and other materials subjected to hardening treatment, and rigid material subjected to lining coating, or plating. In this embodiment, at least a part of the first and the second processing surfaces 1 and 2 is subjected to mirror polished.

(With Regard to Rotation of Processing Surface)

Of the first holder 11 and the second holder 21, at least one of the holders can rotate relative to the other holder by a rotation drive mechanism M such as an electric motor. The drive shaft of the rotation drive mechanism M is connected to a rotation axis 31, in this example, the first holder 11 attached to the rotation axis 31 rotates, the first processing member 10 supported by the first holder 11 rotates relative to the second processing member 20. Of course, the second processing member 20 may be rotated, or both thereof may be rotated.

(With Regard to Approach to and Separate from of Processing Surface)

At least any one of the first processing member 10 and the second processing member 20 are arranged so as to be able to approach to and separated from the at least any one of the other in the axial direction of rotation axis 31, the both processing surfaces 1 and 2 can approach to and separate from each other.

In this embodiment, the first processing member 10 is fixed in the axial direction and is constituted so as to rotate in the circumferential direction.

Incidentally, the second processing member 20 may be disposed on the second holder 21 so as to be only capable of moving parallel in the axial direction, but also may be accommodated with in state of large clearance as well as may hold the second processing member 20 by a floating mechanism which can hold mutable in three dimensions.

(Movement of Fluid to be Processed)

The above-mentioned fluid to be processed is applied pressure by fluid pressure imparting mechanism containing the first fluid pressure imparting mechanism 101 to pressurize the first fluid and the second fluid pressure imparting mechanism 201 to pressurize the second fluid. In this pressurized state, the fluids to be processed containing the first fluid and the second fluid are introduced between the both processing surfaces 1 and 2 from a first introduction part d1 and a second introduction part d2.

In this embodiment, the first introduction part d1 is a flow path by a first pipe 41 arranged in the center of the circular first holder 11, and its downstream end is connected to inside in the radial direction of the circular flow path 3, and introduced between the both processing surfaces 1 and 2.

The second introduction part d2 is a passage provided inside the second processing member 20, one end thereof opens at the second processing surface 2, and this opening becomes a direct introduction opening (second introduction port d20) to the circular flow path 3.

The first fluid is introduced from the first introduction part d1 into the circular flow path 3 through the space of the inner diameter side between the first processing member 10 and the second processing member 20, and the space becomes the first introduction port d10. The first fluid introduced from the first introduction port d10 to the circular flow path 3 becomes a thin film fluid between the first processing surface 1 and the second processing surface 2, and passes through an outside in the radial direction of the first processing member 10 and the second processing member 20. Between these processing surfaces 1 and 2, the second fluid which is pressurized to a predetermined pressure is supplied from the second introduction port d20 of the second introduction part d2, and is joined with the first fluid of a thin film fluid, and a reaction processing is performed while or after performing mixing mainly by molecular diffusion. This reaction processing may be accompanied or may not be accompanied by crystallization, separation or the like.

The thin film fluid by the first fluid and the second fluid is subjected to the fluid processing including reaction processing, and then discharged from the both processing surfaces 1 and 2 to the outside of the both processing members 10 and 20. In this embodiment, by disposing an outer casing 40 at the outside of the both processing members 10 and 20, the fluid to be processed after the reaction processing is efficiently recovered and discharged out of the system.

Incidentally, since the first processing member 10 rotates, the fluid to be processed in the circular flow path 3 moves in substantially spiral form from the inside to the outside as the result of synthetic vector of moving vector in circular radius direction and moving vector in circumferential direction acting on the fluid to be processed, rather than moving linearly from the inside to the outside.

(With Regard to Pressure Balancing Mechanism)

Next, a pressure balancing mechanism will be explained. This pressure balancing mechanism is a mechanism which sets a minute clearance (that is, first clearance) between the two processing surfaces by pressure balance between a pressure applied by the fluid to be processed acting in the direction move away from at least one processing surface and a force provided by back pressure mechanism which acts in the direction approach to the at least one processing surface.

The back pressure mechanism is a mechanism for imparting a force to the processing members to act in the direction of approaching the first processing surface 1 and the second processing surface 2, and in this embodiment, the back pressure mechanism is provided on the second holder 21 and biases the second processing member 20 towards the first processing member 10. The above-mentioned back pressure mechanism is a mechanism to generate force (hereinafter, surface-approaching pressure) to be applied in the direction approaching each other to the first processing surface 1 of the first processing member 10 and the second processing surface 2 of the second processing member 20. By the balance between the surface-approaching pressure and the force to separate the processing surfaces 1 and 2 from each other due to the fluid pressure imparting mechanism (the first fluid pressure imparting mechanism 101 and the second fluid pressure imparting mechanism 201) such as fluid pressure, a thin film fluid having minute thickness in a level of nanometer or micrometer is generated. In other words, the distance between the processing surfaces 1 and 2 is kept in a predetermined minute clearance (the first clearance) by the balance between these forces.

In the embodiment shown in FIG. 1, the back pressure mechanism is arranged between the second holder 21 and the second processing member 20. Specifically, the back pressure mechanism is composed of an elastic material 23 represented by a compression coil spring to bias the second processing member 20 towards the first processing member 10, and a biasing-fluid introduction part (not shown) to introduce a biasing fluid such as air and oil, wherein the surface-approaching pressure is provided by the biasing force of the elastic material 23 and the fluid pressure of the above-mentioned biasing fluid. Any one of the elastic material 23 and the fluid pressure of the above-mentioned biasing fluid may be applied, and also other force such as magnetic force and gravity may be applied.

Against the bias of the back pressure mechanism, according to the separating force generated by the pressure of the fluid to be processed pressurized by the first fluid pressure imparting mechanism 101 and the second fluid pressure imparting mechanism 201 or the viscosity, the second processing member 20 moves away from the first processing member 10, thus a minute space is provided between the both processing surfaces. Thus, by the balance between the surface-approaching pressure and the separating force, the first processing surface 1 and the second processing surface 2 are set the accuracy in a level of μm, then the minute clearance (the first clearance) between the both processing surfaces 1 and 2 is set, a thin film fluid having a minute film thickness in a level of nanometer or micrometer is generated.

The first processing member 10 and the second processing member 20 may incorporate a temperature adjustment mechanism in at least any one of them and may be cooled or heated to adjust the temperature. The heat energy contained in the fluid to be processed having the temperature of cooling or heating may be used for separating the material to be processed which is processed and may also be used for generating Benard convection or Marangoni convection to the fluid to be processed which has become thin film fluid.

(Depression and Micropump Effect)

Figure 2:
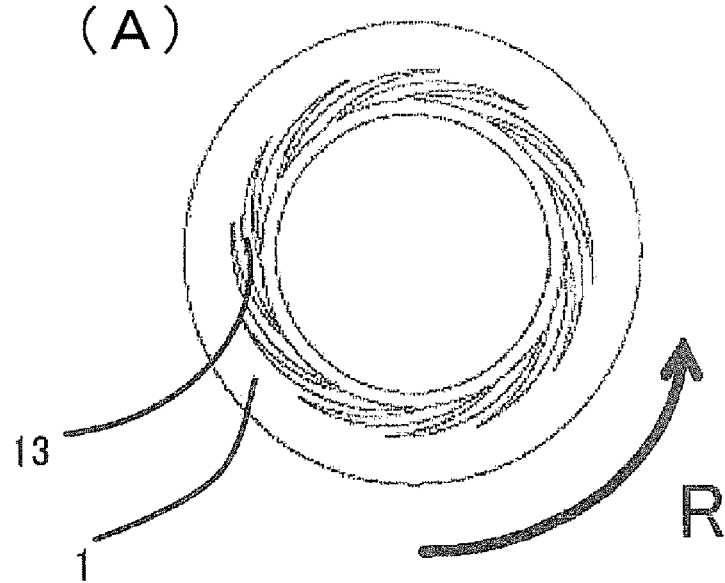
FIG. 2(A) is a schematic plan view of the first processing surface of the fluid processing apparatus shown in FIG. 1.
FIG. 2(B) is an enlarged view of a main part of the processing surface of the apparatus.
Figure 2:
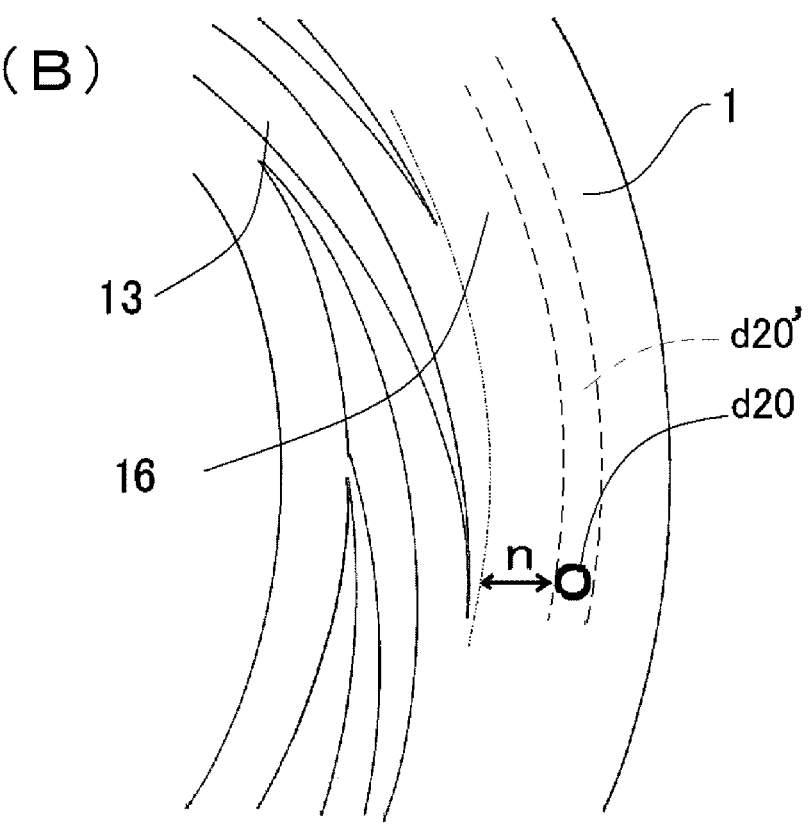

As shown in FIG. 2, in the first processing surface 1 of the first processing member 10, a groove-like depression 13 extended toward an outer side from the central part of the first processing member 10, namely in a radius direction, may be formed. The depression 13 may be, as a plane view, curved or spirally extended on the first processing surface 1 as shown in FIG. 2(B), or, though not shown in the drawing, may be extended straight radially, or bent at a right angle, or jogged; and the depression may be continuous, intermittent, or branched. In addition, this depression 13 may be formed also on the second processing surface 2, or on both the first and second processing surfaces 1 and 2. By forming the depression 13 as mentioned above, the micro-pump effect can be obtained so that the fluid to be processed may be sucked into between the first and second processing surfaces 1 and 2.

It is preferable that the base edge of this depression 13 reach the inner periphery of the first processing member 10.

The front edge of the depression 13 is extended to the direction of the outer periphery of the first processing surface 1; the depth thereof (cross section area) is made gradually shallower (smaller) from the base edge to the front edge.

Between the front edge of the depression 13 and the outer peripheral of the first processing surface 1 is formed the flat plane 16 not having the depression 13.

(With Regard to Rotation Speed and Reaction of Fluid)

It will be described below a preferable position for setting the second introduction port d20 of the above-mentioned second introduction part d2.

when fine particles are to be precipitated from the fluid, it is desirable to perform mixing of a plurality of fluids to be processed by molecular diffusion, and reaction and precipitation of the fine particles under laminar flow conditions. This second introduction port d20 is arranged preferably in the downstream (outside in this case) of the depression 13 of the first processing surface 1. The second introduction port d20 is arranged especially preferably at a position located nearer to the outer diameter than a position where the direction of flow upon introduction by the micro-pump effect is changed to the direction of a spiral and laminar flow formed between the processing surfaces. Specifically, in FIG. 2(B), a distance n from the outermost side of the depression 13 arranged in the first processing surface 1 in the radial direction is preferably about 0.5 mm or more. Especially in the case of separating microparticles from a fluid, it is preferable that mixing of a plurality of fluids to be processed due to molecular diffusion, separation of the microparticles therefrom and reaction be effected under the condition of a laminar flow.

As stated above, in order to process the fluid to be processed under laminar flow conditions, the rotation number of the first processing surface 1 is suitably 200 to 6,000 rpm, more preferably 350 to 5,000 rpm (circumferential velocity on the outer circumference: 1.8 to 39.3 m/sec). In the fluid processing apparatus of the present invention in which the fluid to be processed is reacted as a microreactor, the rotation speed is sufficiently low as compared with the rotation number of 8,000 to 12,000 rpm of the processing surface in a micronization apparatus by shearing. When rotation speed is higher than the above, turbulent flow conditions are obtained, as a result, for example, the encounter of plural kinds of substances contained in the first fluid and the second fluid to be reacted between the processing surfaces 1 and 2 becomes random, thus there is risk that it is difficult to perform uniform reaction or separation of uniform particles.

(With Regard to Second Introduction Part)

The form of the second introduction port d20 may be an independent opening such as a circular as shown in FIG. 2(B) and FIG. 3(B), or may be a continuous opening (see d20' shown by a broken line in FIG. 2(B)) such as a concentric circular ring surrounding the central opening of the processing surface 2 which is a ring-shape disk. In addition, when the second introduction port d20 is circular shaped opening d20', the circular shaped opening part may be continuous through the whole circumference, or a part of which may be discontinuous.

When the circular shaped second introduction port d20 is arranged on concentric circular ring surrounding the central opening of the processing surface 2, at the time of introducing the second fluid between the processing surfaces 1 and 2, the same conditions may be applied in the circumferential direction, so that when it is desired to mass-produce microparticles, the form of the opening may preferably be concentric circular ring.

This second introduction part d2 may have directionality. For example, as shown in FIG. 3(A), the direction of introduction from the introduction port d20 of the second processing surface 2 is inclined at a predetermined elevation angle (θ1) relative to the second processing surface 2. The elevation angle (θ1) is set at more than 0° and less than 90°, and when the reaction speed is high, the angle (θ1) is preferably set in the range of 1° to 45°.

In addition, as shown in FIG. 3(B), when the second introduction port d20 is an independent opening hole, it can be made to have directionality in a plane along the second processing surface 2. The direction of introduction of this second fluid is in the outward direction departing from the center in a radial component of the processing surface and in the forward direction in a rotation component of the fluid between the rotating processing surfaces. In other words, a predetermined angle (θ2) exists facing the rotation direction R from a reference line g, which is the line to the outward direction and in the radial direction passing through the second introduction port d20. This angle (θ2) is also set preferably at more than 0° and less than 90°.

(Kind of Fluid to be Processed and Number of Flow Paths)

In the embodiment shown in FIG. 1, kinds of the fluid to be processed and numbers of the flow path thereof are set two respectively; but they may be one, or three or more. In the embodiment shown in FIG. 1, the second fluid is introduced into between the processing surfaces 1 and 2 from the introduction part d2; but this introduction part may be arranged in the first processing member 10 or in both. Alternatively, a plurality of introduction parts may be arranged relative to one fluid to be processed. Each introduction port is not particularly restricted in its form, size, and number; and these may be changed as appropriate. The introduction port may be arranged just before the first and second processing surfaces 1 and 2 or in the side of further upstream thereof. In addition, the expressions of the first and second in each fluid only have a meaning for identification of being the n-th of a plurality of existing fluids, and third or more fluids may exist. Incidentally, each flow path is sealed as liquid-tight (when the fluid to be processed is liquid) or airtight (when the fluid to be processed is gas).

(Fluid Processing in First Clearance of Present Apparatus)

As described above, in the above-mentioned apparatus, fluid processing is performed as follows in a state where the distance between the first processing surface 1 and the second processing surface 2 is set to be the first clearance.

First, in accordance with necessity, the fluid to be processed before being introduced into the fluid processing apparatus is subjected to a preparation process in which the mixed state and dissolved state are ideally obtained, and temperature adjustment process to set the temperature suitable for the reaction, and then the fluid to be processed is introduced into the apparatus.

When introducing, the fluid to be processed set to predetermined pressure is continuously fed into the fluid processing apparatus and introduced into the circular flow path 3. The fluid to be processed thus introduced passes through the circular flow path 3 between the processing surfaces having minute clearance (first clearance) due to pressure balance, thus realized the homogenous reaction in the thin film fluid, as the result, the excellent effects can be exerted, for example, in the case that the reaction is accompanied with the separation of microparticles, the microparticles having uniform particle diameter can be obtained.

In particular, when the second fluid is joined to the first fluid under laminar flow conditions, and mixing and reaction of the fluids to be processed are performed by molecular diffusion under the above-mentioned laminar flow conditions, the fact that each fluid has homogeneous conditions is the condition that influences a great effect on the homogeneity of the reaction results, and the system of the present invention is effective in the point of satisfying such a condition.

(Kind of Fluid and Reaction)

The fluid processing method by the present apparatus can be applied to various fluids to be processed disclosed in Patent Document 4 and can be applied to various reactions.

Illustrative example thereof shows that the fluid to be mixed is not specifically restricted in the case of feeding the first fluid to be processed which is mixed with the plural kind of the fluid into between the processing surfaces, for example, it is useful in the case of mixing the fluid containing high viscosity or highly viscous material in the any one of the fluids to be processed or in the case of desirably introducing inorganic materials such as oxides, metals, ceramics, semiconductors, and silica, or organic materials such as pigments and drugs intobetween the processing surfaces.

In many cases, they often form aggregates since they are fine, it is desirable to introduce them between the processing surfaces in a uniform state without concentration distribution. In addition, emulsification and dispersing process can be simultaneously carried out with mixing such as mixing of water and oil. In the case of dissolution, for example, when dissolving water-soluble polymers such as cellulose-based water-soluble polymers and hyaluronic acid in water, uniform dissolution treatment can be performed without unevenness in concentration even when concentration distribution or viscosity distribution are occurred by use of general tank or stirrer which the dissolution makes difficult.

In addition, in organic synthesis, even in the case where decomposition occurs or heat is generated by premixing, the reaction can be immediately performed by introducing a material which easily generates a by-product immediately before the reaction.

(Mechanical Clearance Mechanism)

Next, a mechanical clearance mechanism which is a main part of the present invention will be explained.

In this embodiment, the mechanical clearance mechanism is composed of a second elevating holder 51 (second holder 21) and an operation unit 61.

The second elevating holder 51 and the second holder disclosed in Patent Documents 4 and 5 are basically the same, but whereas the conventional second holder is fixed on the apparatus main body, the second holder 21 of the present invention moves up and down. In order to clarify this point, the second elevating holder 51 will be explained as follows, but the same member with the above-mentioned second holder 21 is shown. Accordingly, in FIG. 1 and FIG. 4, two reference numerals 21 and 51 are put down with.

The operation unit 61 is a member that moves up and down due to the rotation relative to an outer casing 40, and is practiced as a cylindrical body having a female screw 63 at the bottom part. This female screw 63 is screwed into a male screw 43 provided in the outer casing 40. The male screw 43 is formed on the outer periphery of a Cylindrical part 44 provided so as to be capable of extending upward from the upper part of the outer casing 40. Accordingly, by rotating the operation unit 61, the operation unit 61 moves up and down with respect to the outer casing 40 along the direction of the rotation axis of the first processing surface 1.

The second elevating holder 51 is provided so as to be incapable of rotating but be capable of elevating to the outer casing 40. This second elevating holder 51 non-rotatably moves up and down to the outer casing 40 by rotating the operation unit 61. To explain specifically, the second elevating holder 51 is arranged inside the operation unit 61 and the Cylindrical part 44. Also, the second elevating holder 51 is connected to the operation unit 61 by a transmission engaging part 52 which is slidably inserted relative to a transmission Receiving part 62 provided in the operation unit 61. Accordingly, the second elevating holder 51 is to be arranged relative to the operation unit 61 so as to be rotatable and not to be elevated in relation to the operation unit 61. In addition, the second elevating holder 51 is connected to the Cylindrical part 44 so as to be incapable of rotating but to be capable of moving up and down by a slide part 53 such as a keyway structure in the outer periphery. As a result, when the operation unit 61 is rotated, the second elevating holder 51 also moves up and down as well as rotates according to the movement thereof, but since the slide part 53 is not rotatable, the second elevating holder 51 moves up and down linearly along the direction of the rotation axis of the first processing surface 1, and the second elevating holder 51 is mechanically moved towards and away from the second processing member 20.

This second elevating holder 51 also serves as a spring receiver on the upper side of the back pressure mechanism, and by moving the second elevating holder 51 downward, the second processing member 20 moves downward via the elastic body 23. On the other hand, when the second elevating holder 51 moves upward, by being connected the second processing member 20 and the second elevating holder 51 via an ascending transmission part 54, the second processing member 20 moves upward. Specifically, the ascending transmission part 54 is extended downward from the second elevating holder 51, and an engaging part 55 is provided at the lower part of the ascending transmission part 54. A Receiving part 24 is provided in the second processing member 20, and in the Receiving part 24, lower part of the ascending transmission part 54 is disposed so as to be capable of elevating. The Receiving part 24 is provided with a part to be engaged 25 with a small diameter at an upper part thereof, and the engaging part 55 of the ascending transmission part 54 engages to the part to be engaged 25 from downward. More specifically, a bolt can be used as the ascending transmission part 54, and it can be practiced by screwing the shaft portion to the second elevating holder 51, and the head part thereof as the engaging part 55.

Accordingly, when the ascending transmission part 54 moves upward accompanied with the ascending of the second elevating holder 51, the engaging part 55 engages with the part to be engaged 25, thus, the second processing member 20 moves upward so as to lift up. Incidentally, even when the ascending transmission part 54 moves downward accompanied with the descending of the second elevating holder 51, the engaging part 55 merely moves downward in the Receiving part 24, which does not directly affect vertical movement of the second processing member 20.

Incidentally, second pipe 42 which constitutes the second introduction part d2 is penetrated in the second elevating holder 51 which leaves some space and does not influenced by the movement of the second elevating holder 51.

As shown in FIG. 4, a cleaning sterilization flow path 45 into which at least any one of a cleaning liquid and steam for sterilization for CIP or SIP is introduced the apparatus is provided on the outer casing 40. On the contrary, on the outer peripheral side of the surface of the second processing member 20, an upper sealing part 46 and a lower sealing part 47 such as O-ring is provided with an interval in the vertical direction.

When being set on the first clearance, by positioning the cleaning sterilization flow path 45 between the upper sealing part 46 and the lower sealing part 47, the cleaning sterilization flow path 45 is not connected to the circular flow path 3. On the other hand, when being set on the second clearance, by positioning the cleaning sterilization flow path 45 the lower side of the lower sealing part 47, the cleaning sterilization flow path 45 and the circular flow path 3 are connected, whereby cleaning and/or sterilization to each part such as the first and second processing surfaces 1 and 2 and the circular flow path 3 can be performed.

(Processing in First Clearance)

The processing to the fluid to be processed in the first clearance is as explained in the detail above, thus not repeated here, however, the set value of the first clearance may be adjusted by a mechanical clearance mechanism. As described above, by the balance between the separating force and the surface-approaching pressure, the first clearance is adjusted, however, when the surface-approaching pressure is applied by the elastic material 23, the distance to the second processing member 20 is changed by elevating the second elevating holder 51, as the result, the biasing force of the elastic material 23 to the second processing member 20 (and hence the second processing surface 2) changes. According to the above, even when the other separating force and the surface-approaching pressure are maintained under the same conditions, the surface-approaching pressure is changed only by the elevating of the second elevating holder 51, and then the set value of the first clearance is changed.

Specifically, by rotating the operation unit 61 forward (rotating clockwise direction as viewed from upper side of FIG. 1), the operation unit 61 moves downward while rotating. The second elevating holder 51 to which is connected the operation unit 61 by the transmission receiving part 62 and the transmission engaging part 52 moves downward without rotating due to the action of the slide part 53. According to the above, the distance between the second elevating holder 51 and the second processing member 20 becomes small, and the biasing force of the elastic material 23 is increased accordingly, and the surface-approaching pressure is increased. By reversely rotating the operation unit 61 to the other side, the movement is reversed, thereby the surface-approaching pressure is decreased. Incidentally, the expression of forward and reverse is merely used for convenience, when the rotation is made in the counterclockwise direction as viewed of FIG. 1 from upper side, it does not prevent the execution that the operation unit 61 moves downward while rotating.

Of course, in the first clearance, the above-mentioned adjustment by the mechanical clearance mechanism is not essential, and the set value of the first clearance may be adjusted by changing the other separating force and the surface-approaching pressure in a state where the second elevating holder 51 is stopped at a predetermined position. Also, in order not to carelessly change the position of the second elevating holder 51, the operation unit 61 or the second elevating holder 51 may be constituted so as to be fixed with a releasable lock mechanism and the like.

Incidentally, when it is set on the first clearance, the cleaning sterilization flow path 45 is not connected to the circular flow path 3 by positioning the cleaning sterilization flow path 45 between the upper sealing part 46 and the lower sealing part 47, so that processing of the fluid to be processed can be executed in a state where the fluid for cleaning or sterilization is interrupted from.

(Processing in Second Clearance)

Next, a case where the first clearance is changed to the second clearance will be explained. This second clearance is set for the purpose of performing CIP or SIP of the apparatus, but it may be also set in operations for other purposes in such case that adhered material is to be removed by introducing dissolving liquid when processed material or reaction product in the fluid to be processed is adhered to the processing surface.

When shifting from the first clearance to the second clearance, the second elevating holder 51 is raised. Specifically, the operation unit 61 is reversely rotated. According to this procedure, the operation unit 61 rises while rotating. The second elevating holder 51 to which is connected the operation unit 61 by the transmission receiving part 62 and the transmission engaging part 52 moves upward without rotating by the action of the slide part 53. By this, the distance between the second elevating holder 51 and the second processing member 20 becomes large. The biasing force of the elastic material 23 becomes small due to the increase of the distance, but with this alone, the second processing member 20 does not rise unless the separating force such as a pressure of the fluid to be processed, as in the first clearance mentioned above, the clearance will be the state that depends on the pressure of the fluid to be processed.

On the contrary, in the present apparatus, the ascending transmission part 54 is provided, as the result, the second processing member 20 and the second processing surface 2 can be pulled up to the position of the second clearance. Specifically, by ascending the second elevating holder 51, the engaging part 55 of the ascending transmission part 54 engages with the part to be engaged 25 of the Receiving part 24 arranged in the second processing member 20. According to this engagement, the second processing member 20 moves upward together with the second elevating holder 51. Thus, the second clearance can be set by the mechanical clearance mechanism irrespective of the presence or absence of the pressure of the fluid to be processed or its values. Incidentally, the elastic material 23 may be in a free state where the biasing force is not applied between the second processing member 20 and the second elevating holder 51 in the second clearance, or may be in a contraction state where the biasing force is applied. In other words, even in the position of the second clearance, the pressure balancing mechanism may be in a state of effectively acting, or may be in a state of not acting effectively.

Incidentally, since the second processing member 20 is in a floating state relative to the inner surface of the outer casing 40, as shown in FIG. 4, when it is set to the second clearance, the second processing member 20 is raised, and as a result, by positioning the cleaning sterilization flow path 45 at lower side of the lower sealing part 47, the cleaning sterilization flow path 45 and the circular flow path 3 are connected. By this, the fluid for cleaning or sterilization can flow from the cleaning sterilization flow path 45 to the inside of the fluid processing apparatus (including the part where the fluid to be processed flows in the processing step of the fluid to be processed), whereby CIP or SIP can be performed smoothly. Incidentally, the fluid for cleaning or sterilization may be fed from first pipe 41 or second pipe 42. The fluid for cleaning or sterilization is flown out to the outside of the outer casing 40 similarly to the fluid to be processed, but the fluid for cleaning or sterilization is made to flow backward and then can be flown out from the cleaning sterilization flow path 45, the first pipe 41 or the second pipe 42.

Modified Example

The present invention should not be understood as being limited to the above-mentioned embodiments, and can be executed with various modifications.

For example, although the means for rotating the second elevating holder 51 is not particularly explained, the second elevating holder 51 may be directly manually rotated, or may be rotated manually or by the other power source via the other rotation connecting means. The operation unit 61 is moved up and down by screwing the male screw 43 and the female screw 63, but when more precise adjustment is required, a plurality of rotational force transmitting means such as a gear can be used. A linear precision moving means such as a ball screw may also be used instead of moving up and down by screwing the male screw 43 and the female screw 63. On the other hand, when precise adjustment is not required, moving means such as rack and pinion may be used.

In addition, the mechanical clearance mechanism for obtaining the second clearance may be provided on near the first processing surface 1 and the first processing member 10. That is, it may be executed by that the pressure balancing mechanism is provided on near the second processing surface 2 and the second processing member 20, and the mechanical clearance mechanism is provided on near the first processing surface 1 and the first processing member 10.

EXPLANATION OF REFERENCE NUMERALS

1 First processing surface
2 Second processing surface
3 Circular flow path
10 First processing member
11 First holder
13 Depression
20 Second processing member
21 Second holder
51 Second elevating holder
23 Elastic material
24 Receiving part
25 Part to be engaged
31 Rotation axis
40 Outer casing
41 First pipe
42 Second pipe
43 Male screw
44 Cylindrical part
45 Cleaning sterilization flow path
46 Upper sealing part
47 Lower sealing part
52 Transmission engaging part
53 Slide part
54 Ascending transmission part
55 Engaging part
61 Operation unit
62 Transmission Receiving part
63 Female screw
101 First fluid pressure imparting mechanism
201 Second fluid pressure imparting mechanism
d1 First introduction part
d10 First introduction port
d2 Second introduction part
d20 Second introduction port

The invention claimed is:

1. A forced thin film-type flow reactor for processing a fluid to be processed comprising:
   two processing surfaces disposed so as to be relatively capable of moving toward and away from each other,
   a pressure balancing mechanism which forms a minute first clearance between the two processing surfaces by a pressure balance between imparted pressure of the fluid to be processed which acts in a direction of move away from at least one of the processing surfaces and a force due to a back pressure mechanism which acts in a direction of approaching to the at least one of the processing surfaces, and
   a mechanical clearance mechanism which mechanically sets a second clearance being greater than the first clearance between the two processing surfaces.

2. The forced thin film-type flow reactor according to claim 1, wherein a cleaning and sterilization flow path for CIP or SIP capable of being connectable between the two processing surfaces is provided, and
   wherein the cleaning and sterilization flow path is set to a closed position in the first clearance and open position in the second clearance in accordance with approaching to and separating from at least one of the processing surfaces.

3. The forced thin film-type flow reactor according to claim 1, wherein the first clearance set by the pressure balancing mechanism is in the range of 0.5 to the second clearance set by the mechanical clearance mechanism is in the range of 50 µm to 4 mm, and
   wherein the mechanical clearance mechanism is configured to be able to set the second clearance to be greater than the first clearance which is set by the pressure balancing mechanism irrespective of the pressure of the fluid being passed between the two processing surfaces.

4. The forced thin film-type flow reactor according to claim 1, wherein
   a first processing member is provided with a first processing surface of the two processing surfaces and a second processing member is provided with a second processing surface of the two processing surfaces, the first processing surface and the second processing surface facing opposite to each other,
   wherein the second processing member is connected to a second holder via back pressure mechanism so as to be able to approach to and separate from the first processing member, the second processing member is arranged so as to approach to the first processing member due to the separation from the second holder and separate from the first processing member due to the approach to the second holder,
   wherein the second holder is a second elevating holder which approaches to and separates from the first processing member, and
   wherein the mechanical clearance mechanism is configured in such a manner that the second elevating holder is mechanically moved so as to approach to and separated from the first processing member as well as, in a case where the second elevating holder moves in the direction of separating from the first processing member, the second processing member together with the second elevating holder is mechanically moved in the direction of mechanically separating from the first processing member.

5. A method for operating a forced thin film-type flow reactor, wherein in the method for operating the forced thin film-type flow reactor according to claim 1,
when processing a material to be processed, processing of the fluid to be processed is performed by passing the fluid to be processed between the two processing surfaces set for the first clearance,
wherein at the time of CIP or SIP of the forced thin film-type flow reactor, CIP or SIP is executed by the second clearance.

6. The forced thin film-type flow reactor according to claim 2, wherein the first clearance set by the pressure balancing mechanism is in the range of 0.5 to 50 μm, the second clearance set by the mechanical clearance mechanism is in the range of 50 μm to 4 mm, and
wherein the mechanical clearance mechanism is configured to be able to set the second clearance to be greater than the first clearance which is set by the pressure balancing mechanism irrespective of the pressure of the fluid being passed between the two processing surfaces.

7. The forced thin film-type flow reactor according to claim 2, wherein a first processing member is provided with a first processing surface of the two processing surfaces and a second processing member is provided with a second processing surface of the two processing surfaces, the first processing surface and the second processing surface facing opposite to each other,
wherein the second processing member is connected to a second holder via back pressure mechanism so as to be able to approach to and separate from the first processing member, the second processing member is arranged so as to approach to the first processing member due to the separation from the second holder and separate from the first processing member due to the approach to the second holder,
wherein the second holder is a second elevating holder which approaches to and separates from the first processing member, and
wherein the mechanical clearance mechanism is configured in such a manner that the second elevating holder is mechanically moved so as to approach to and separated from the first processing member as well as, in a case where the second elevating holder moves in the direction of separating from the first processing member, the second processing member together with the second elevating holder is mechanically moved in the direction of mechanically separating from the first processing member.

8. The forced thin film-type flow reactor according to claim 3, wherein a first processing member is provided with a first processing surface of the two processing surfaces and a second processing member is provided with a second processing surface of the two processing surfaces, the first processing member and the second processing member facing opposite to each other,
wherein the second processing member is connected to a second holder via back pressure mechanism so as to be able to approach to and separate from the first processing member, the second processing member is arranged so as to approach to the first processing member due to the separation from the second holder and separate from the first processing member due to the approach to the second holder,
wherein the second holder is a second elevating holder which approaches to and separates from the first processing member, and
wherein the mechanical clearance mechanism is configured in such a manner that the second elevating holder is mechanically moved so as to approach to and separated from the first processing member as well as, in a case where the second elevating holder moves in the direction of separating from the first processing member, the second processing member together with the second elevating holder is mechanically moved in the direction of mechanically separating from the first processing member.

9. A method for operating a forced thin film-type flow reactor, wherein in the method for operating the forced thin film-type flow reactor according to claim 2,
when processing a material to be processed, processing of the fluid to be processed is performed by passing the fluid to be processed between the two processing surfaces set for the first clearance,
wherein at the time of CIP or SIP of the forced thin film-type flow reactor, CIP or SIP is executed by the second clearance.

10. A method for operating a forced thin film-type flow reactor, wherein in the method for operating the forced thin film-type flow reactor according to claim 3,
when processing a material to be processed, processing of the fluid to be processed is performed by passing the fluid to be processed between the two processing surfaces set for the first clearance,
wherein at the time of CIP or SIP of the forced thin film-type flow reactor, CIP or SIP is executed by the second clearance.

11. A method for operating a forced thin film-type flow reactor, wherein in the method for operating the forced thin film-type flow reactor according to claim 4,
when processing a material to be processed, processing of the fluid to be processed is performed by passing the fluid to be processed between the two processing surfaces set for the first clearance,
wherein at the time of CIP or SIP of the forced thin film-type flow reactor, CIP or SIP is executed by the second clearance.

12. A method for operating a forced thin film-type flow reactor, wherein in the method for operating the forced thin film-type flow reactor according to claim 1, wherein the two processing surfaces comprise a first processing surface and a second processing surface, and
wherein the first processing surface is fixed in an axial direction, and the second processing surface can move toward and away from the first processing surface.

13. A forced thin film-type flow reactor for processing a fluid to be processed comprising:
two processing surfaces comprising a first processing surface and a second processing surface disposed so as to be relatively capable of moving toward and away from each other;
an outer casing encircling the two processing surfaces;
an operator movable in an axial direction relative to the outer casing;
a plate fixed in the axial direction to the operator, the plate extending across a top of the operator and above the second processing surface which mechanically sets a clearance being between the two processing surfaces; and
a spring between the plate and second processing surface, the spring opposing pressure of the fluid between the two processing surfaces.

14. The forced thin film-type flow reactor according to claim 13, wherein the operator and outer casing are connected by mating screw threads so that the operator rotates and moves axially relative to the outer casing.

15. The forced thin film-type flow reactor according to claim 13, wherein the operator can rotate relative to the plate.

16. The forced thin film-type flow reactor according to claim 13, wherein the plate fits with a groove in an inner surface of the operator.

17. The forced thin film-type flow reactor according to claim 13, wherein a first processing member is provided with a first processing surface of the two processing surfaces and a second processing member is provided with a second processing surface of the two processing surfaces, and further comprising a bolt having a threaded rod engaging the plate and a head retained in a recess in the second processing member.

* * * * *